(12) United States Patent
Hiraoka et al.

(10) Patent No.: US 8,071,363 B2
(45) Date of Patent: Dec. 6, 2011

(54) CHIP FOR CELL ELECTROPHYSIOLOGICAL SENSOR, CELL ELECTROPHYSIOLOGICAL SENSOR USING THE SAME, AND MANUFACTURING METHOD OF CHIP FOR CELL ELECTROPHYSIOLOGICAL SENSOR

(75) Inventors: Soichiro Hiraoka, Osaka (JP); Masaya Nakatani, Hyogo (JP); Hiroshi Ushio, Hyogo (JP); Akiyoshi Oshima, Osaka (JP)

(73) Assignee: Panasonic Corporation, Osaka (JP)

( * ) Notice: Subject to any disclaimer, the term of this patent is extended or adjusted under 35 U.S.C. 154(b) by 410 days.

(21) Appl. No.: 11/914,283

(22) PCT Filed: May 21, 2007

(86) PCT No.: PCT/JP2007/060326
§ 371 (c)(1),
(2), (4) Date: Nov. 13, 2007

(87) PCT Pub. No.: WO2007/138902
PCT Pub. Date: Dec. 6, 2007

(65) Prior Publication Data
US 2009/0152110 A1    Jun. 18, 2009

(30) Foreign Application Priority Data

May 25, 2006  (JP) ................. 2006-144801
Jan. 31, 2007  (JP) ................. 2007-020834

(51) Int. Cl.
 *C12M 1/34* (2006.01)
(52) U.S. Cl. .................. 435/287.2; 205/777.5; 257/646

(58) Field of Classification Search ............... 435/287.2; 205/777.5; 257/646
See application file for complete search history.

(56) References Cited

U.S. PATENT DOCUMENTS

| 5,183,744 | A | 2/1993 | Kawamura et al. |
| 6,682,649 | B1 | 1/2004 | Petersen et al. |
| 6,984,297 | B2 | 1/2006 | Nisch et al. |
| 7,006,929 | B2 | 2/2006 | Oka et al. |
| 7,501,278 | B2 | 3/2009 | Nakatani et al. |
| 2003/0113833 | A1 | 6/2003 | Oka et al. |
| 2004/0033483 | A1 | 2/2004 | Oka et al. |
| 2005/0212095 | A1* | 9/2005 | Vestergaard et al. ......... 257/646 |

(Continued)

FOREIGN PATENT DOCUMENTS
EP         0 652 308 A2    10/1994
(Continued)

OTHER PUBLICATIONS

Machine translation from Japanese to English of JP 2004-271330, A.*

(Continued)

*Primary Examiner* — Jeffrey T Barton
*Assistant Examiner* — J. Christopher Ball
(74) *Attorney, Agent, or Firm* — RatnerPrestia

(57) ABSTRACT

A chip for a cell electrophysiological sensor has a substrate. The substrate has a through-hole formed from the upside to the downside, and the opening of the through-hole is formed in a curved surface curved from the upside and downside of the substrate toward the inner side of the through-hole. In this configuration, the electrolyte solution (first electrolyte solution and second electrolyte solution) flows more smoothly, and the sample cell can be sucked accurately, and the trapping rate of the sample cells is improved.

19 Claims, 13 Drawing Sheets

U.S. PATENT DOCUMENTS

2005/0221469 A1    10/2005    Nakatani et al.

FOREIGN PATENT DOCUMENTS

| JP | 2-131569 A | 5/1990 |
|----|----|----|
| JP | 06-244257 A | 9/1994 |
| JP | 2003-511668 A | 3/2003 |
| JP | 2003-511699 A | 3/2003 |
| JP | 2003-511699 A | 3/2003 |
| JP | 2004-12215 A | 1/2004 |
| JP | 2004-69309 A | 3/2004 |
| JP | 2004-271330 A | 9/2004 |
| JP | 2004-271331 A | 9/2004 |
| JP | 2005-156234 A | 6/2005 |
| WO | WO 01/27614 A1 | 4/2001 |
| WO | WO 02/055653 A1 | 7/2002 |
| WO | WO 02/055653 A1 | 7/2002 |
| WO | WO 02/099408 A1 | 12/2002 |
| WO | WO 03/016555 A1 | 2/2003 |

OTHER PUBLICATIONS

JP Office Action for 2010-186807, Mar. 29, 2011.
Japanese Search Report for Application No. PCT/JP2007/060326, dated Aug. 28, 2007.
English translation of Form PCT/ISA/210, Aug. 28, 2007.

* cited by examiner

னCHIP FOR CELL
ELECTROPHYSIOLOGICAL SENSOR, CELL
ELECTROPHYSIOLOGICAL SENSOR USING
THE SAME, AND MANUFACTURING
METHOD OF CHIP FOR CELL
ELECTROPHYSIOLOGICAL SENSOR

This Application is a U.S. National Phase Application of PCT International Application PCT/JP2007/060326.

TECHNICAL FIELD

The present invention relates to a chip used in cell electrophysiological sensor for measuring electrophysiological activities of cells, a cell electrophysiological sensor using this chip, and a manufacturing method of chip for cell electrophysiological sensor.

BACKGROUND ART

As a method of measuring ion channels depending on cell membrane electrophysiologically, a substrate type probe making use of ultrafine processing technology has been noticed. Unlike the conventional micropipette, it does not require skilled operation for inserting a micropipette into individual cells, and it is suited to an automated system of high throughput.

For example, as shown in FIG. 26, the existing cell electrophysiological sensor 1 (substrate probe) includes a substrate 2 and an electrode jar 3 disposed above the substrate 2. The substrate 2 has a through-hole 5 penetrating through the substrate 2 from its upside to downside.

Inside of the electrode jar 3, a first electrode 6 is disposed, and a second electrode 7 is disposed inside of the through-hole 5. The second electrode 7 is coupled to a signal detector (not shown) by way of a wiring 8.

The operating method of the cell electrophysiological sensor 1 is explained below.

First, an electrolyte solution 9 and a sample cell 10 are poured into the electrode jar 3. The sample cell 10 is trapped and held at an opening 4 of the through-hole 5.

At the time of measurement, the sample cell 10 is sucked by a suction pump or the like from beneath the through-hole 5, and is held in contact with the opening 4. This through-hole 5 plays the same role as the leading end hole in the micropipette. The function and pharmacological reaction of the ion channel of the sample cell 10 are analyzed by measuring the voltage or current before and after reaction between the first electrode 6 and second electrode 7, and determining the potential difference inside and outside of the cell (see, for example, patent document 1).

However, in the conventional cell electrophysiological sensor 1, the flow of electrolyte solution 9 flowing in and out of the through-hole 5 is poor, and the rate of trapping the sample cell 10 is low.

Since the through-hole 5 is very fine, and the flow passage suddenly changes in the sectional area at the interface of electrode jar 3 and through-hole 5, and the resistance loss of the fluid increases. As a result, the sample cell 10 cannot be sucked accurately, and the trapping rate declines.

[Patent document 1] International Patent Application Laid-Open No. WO02/055653 pamphlet

DISCLOSURE OF THE INVENTION

The invention is intended to encourage the flow of electrolyte solution flowing in and out of the through-hole, and to enhance the trapping rate of sample cells.

Accordingly, the invention has the through-hole penetrating through the substrate from its upside to downside, in which the inner wall of the through-hole and the substrate surface are linked on a curved surface.

As a result, the electrolyte solution flows easily in and out of the through-hole, and the trapping rate of sample cells can be enhanced.

Specifically, the opening of the through-hole is formed in a curved surface smoothly linking with the substrate surface, and changes of sectional area of passage from the electrode jar to the inside of the through-hole are moderate, and the resistance loss of fluid is decreased. Hence, the electrolyte solution is allowed to flow easily in and out of the through-hole, and the sample cell is trapped accurately, and the trapping rate is enhanced.

DESCRIPTION OF THE REFERENCE NUMERALS

Figure 1:
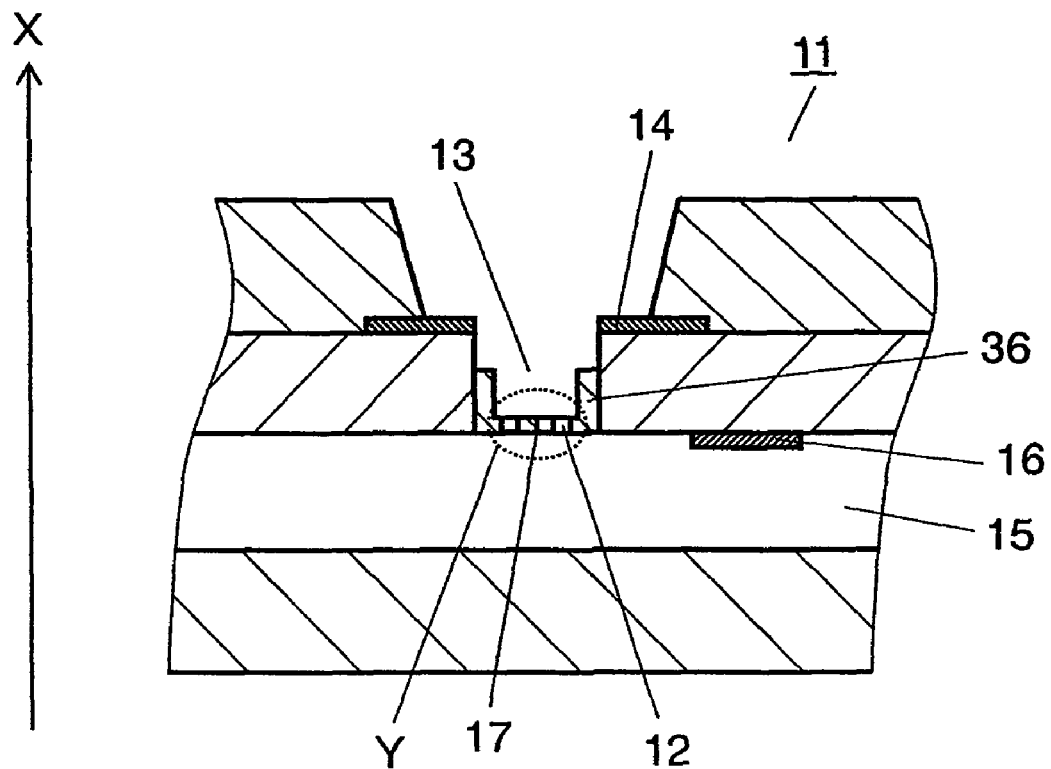
FIG. 1 is a sectional view of cell electrophysiological sensor in a preferred embodiment of the invention.

11 Cell electrophysiological sensor
12 Substrate
13 First electrode jar
14 First electrode
15 Second electrode jar
16 Second electrode
17 Through-hole
17A, 17B, 17C, 17D Opening
18, 18A, 18B Bulge
19 Sample cell
20 First electrolyte solution
21 Second electrolyte solution
22 Resist mask
23 Mask hole
24 Insulation layer
25 Oxide layer
26 Silicon layer
27 Block
28 Resist mask
29 Resist mask
30 Hole
31 Insulation layer
32 Recess
32A Opening
33 Resist mask
34 Mask hole
35 Intersection
36 Chip

DETAILED DESCRIPTION OF THE PREFERRED EMBODIMENTS

Preferred Embodiment 1

Figure 3:
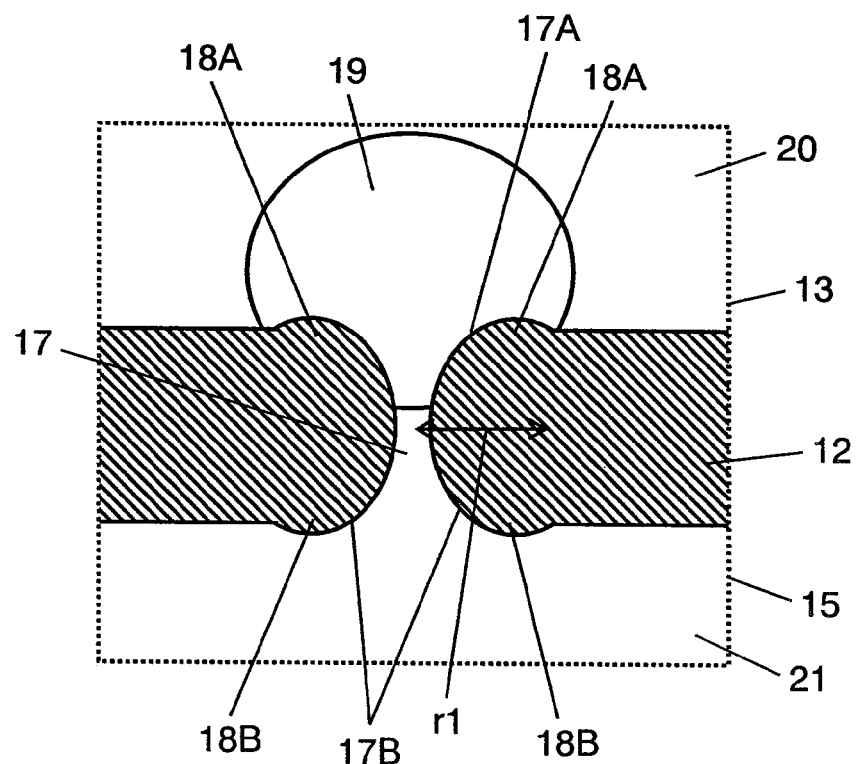
FIG. 3 is an essential magnified sectional view of operation of cell electrophysiological sensor in a preferred embodiment of the invention.
Figure 4:
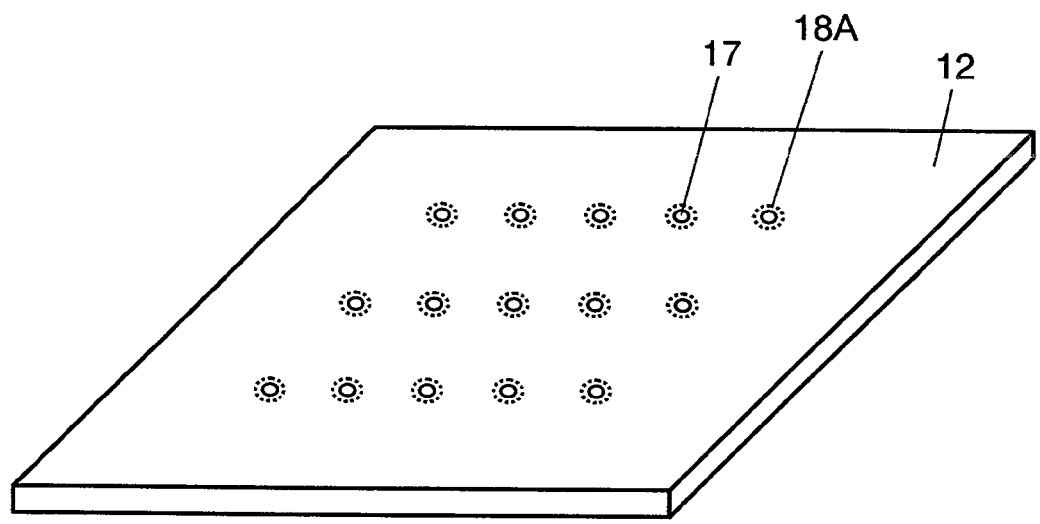
FIG. 4 is a perspective view of substrate in a preferred embodiment of the invention.

A cell electrophysiological sensor in preferred embodiment 1 of the invention is described while referring to the drawings. FIG. 1 is a sectional view of cell electrophysiological sensor in preferred embodiment 1, FIG. 2 is a sectional view of a substrate used therein, FIG. 3 is an essential magnified sectional view of operation of the cell electrophysiological sensor, FIG. 4 is a perspective view of the substrate.

In the preferred embodiments explained below, the upper direction refers to the direction of arrow X in FIG. 1.

As shown in FIG. 1, the cell electrophysiological sensor 11 in preferred embodiment 1 includes a chip 36 having a substrate 12, a first electrode jar 13 disposed above the substrate 12, a first electrode 14 disposed inside of the first electrode jar 13 and on the upside of the substrate 12, a second electrode jar 15 disposed beneath the substrate 12, and a second electrode 16 disposed inside of the second electrode jar 15 and on the downside of the substrate 12, and a through-hole 17 penetrates through the substrate 12 from its upside to downside.

Figure 2:
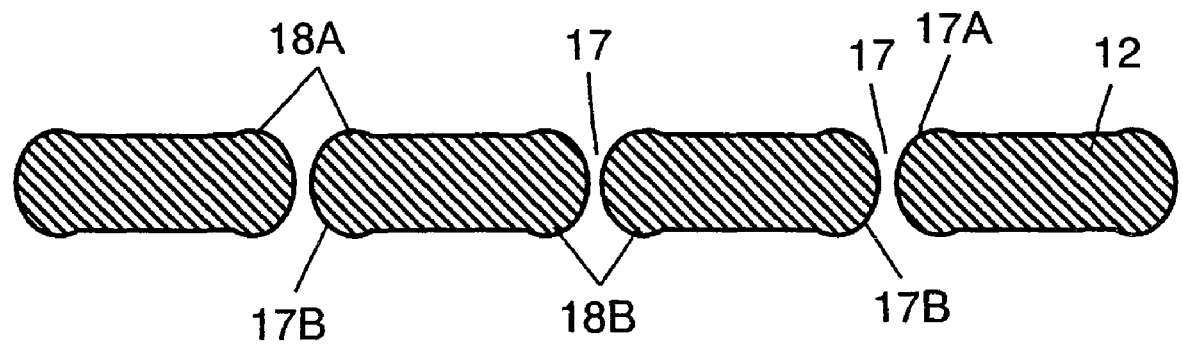
FIG. 2 is a sectional view of substrate (part Y in FIG. 1) in a preferred embodiment of the invention.

The part Y surrounded by dotted line in FIG. 1 is magnified in FIG. 2, in which openings 17A, 17B are curved from the upside and downside of the substrate 12 toward the inner side of the through-hole 17, and are formed in a smooth curved surface linking to the inside of the through-hole 17.

The inner wall of the through-hole 17 is curved to the inner side of the through-hole 17, and is formed in a smooth curved surface projecting nearly at the central point in the depth direction of the through-hole 17.

The aperture of the through-hole 17 is the minimum inside diameter at the central point or near the central point in the depth direction of the through-hole 17, and is gradually increased toward the openings 17A, 17B.

In this preferred embodiment, the outer circumference of the openings 17A, 17B has bulges 18A, 18B smoothly building up on the surface of the substrate 12. As shown in sectional view in FIG. 3, the bulge 18A is formed on the substrate 12 so that the distance r1 from the outermost circumference of the bulge 18A to the center of the opening 17A may be shorter than the radius of the sample cell 19.

In the preferred embodiment, each surface shape of openings 17A, 17B, inner wall of through-hole 17, and bulges 18A, 18B is defined in a smoothness of square average roughness of Rq=1.0 nm or less. The square average roughness of Rq is defined by the square root of average values of square of deviation from the average to the measured value. The radius of sample cell 19 was measured by impregnating the sample cell 19 in physiological saline, and waiting until the osmotic pressure inside and outside the cell was balanced.

The substrate 12 of the chip 36 is a silicon substrate 12, and as shown in FIG. 4, a plurality of through-holes 17 are formed in the substrate 12. The minimum inside diameter of the through-hole 17 is 3 μm.

The inside diameter of the through-hole 17 can be determined depending on the size, shape or properties of the cell to be measured. For example, when the size of the sample cell 19 is about 5 to 50 μm, in order to enhance the contact tightness between the sample cell 19 and opening 17A, the minimum inside diameter of the through-hole 17 is preferred to be 3 μm or less. The depth of the through-hole 17 is 15 μm or less.

The operation of the cell electrophysiological sensor 11 of the invention is described.

As shown in FIG. 3, the first electrode jar 13 is filled with first electrolyte solution 20 (cell outer fluid) containing the sample cell 19, and the second electrode jar 15 is filled with second electrolyte solution 21 (cell inner fluid). By pressurizing from the upside of the substrate 12 or by decompressing the downside, the sample cell 19 and first electrolyte solution 20 are sucked into the through-hole 17. As a result, the sample cell 19 is held as to block the through-hole 17.

In preferred embodiment 1, the sample cell 19 is a mammal muscular cell, the first electrolyte solution 20 is an electrolyte solution containing $K^+$ ions by about 4 mM, $Na^+$ ions by about 145 mM, and $Cl^-$ ions by about 123 mM, and the second electrolyte solution 21 is an electrolyte solution containing $K^+$ ions by about 155 mM, $Na^+$ ions by about 12 mM, and $Cl^-$ ions by about 4.2 mM. Meanwhile, the same composition may be used for the first electrolyte solution 20 and second electrolyte solution 21.

By sucking from the downside of the substrate 12, or by administering a medicine (e.g. Nystatin) from beneath the substrate 12, a fine pore can be formed in the sample cell 19.

A stimulating action on the sample cell 19 is applied from above the substrate 12. Stimulation includes many varieties, such as chemical drug, poison, other chemical simulation, mechanical dislocation, light, heat, electricity, electromagnetic wave, and other physical simulation.

If the sample cell 19 reacts actively to such stimulation, for example, the sample cell 19 releases or absorbs various ions through a channel of cell membrane. As a result, the potential gradient inside and outside the cell is changed, and the change is detected by the first electrode 14 and second electrode 16 shown in FIG. 1, and, for example, the pharmacological reaction of the cell can be studied.

A manufacturing method of cell electrophysiological sensor 11 in preferred embodiment 1 of the invention is explained by referring to the drawings. FIG. 5 to FIG. 9 are sectional views for explaining the manufacturing method of the substrate 12 of the cell electrophysiological sensor 11, and FIG. 10 is a perspective view thereof.

Figure 5:
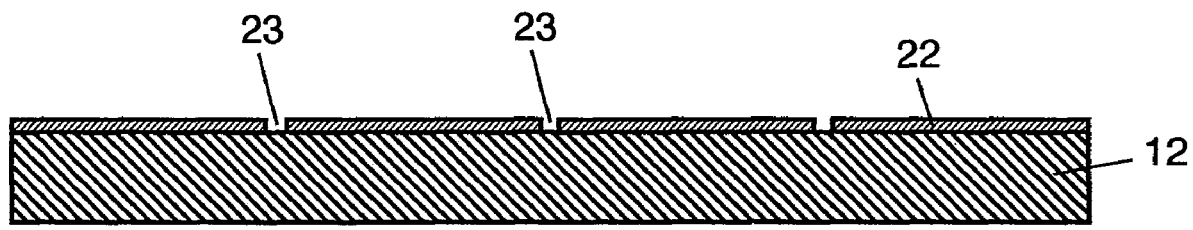
FIG. 5 is a sectional view of manufacturing process of substrate in a preferred embodiment of the invention.

First, as shown in FIG. 5, a resist mask 22 is formed on the upside of the silicon substrate 12. At this time, a mask hole 23 of almost same shape as the section of the desired through-hole 17 is patterned.

Next, by etching the substrate 12, a through-hole is formed (17 in FIG. 2). At this time, the etching method is preferred to be dry etching capable of processing finely at high precision. In the case of dry etching, in order to form a through-hole 17 of high aspect ratio, etching promoting gas (etching gas) and etching suppressing gas (suppressing gas) are used alternately.

In preferred embodiment 1, $SF_6$ is used as etching gas, and $C_4F_8$ is used as suppressing gas.

The dry etching process is specifically described below.

Figure 6A:
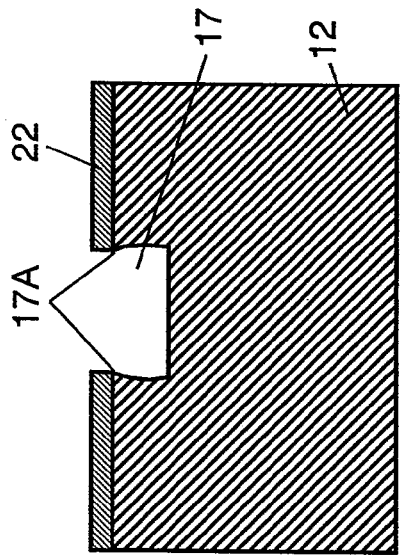
FIG. 6A is an essential sectional view of substrate in a preferred embodiment of the invention.

Above the substrate 12 in FIG. 6A, plasma is generated by induction coupling method of external coil, and $SF_6$ is introduced as etching gas, and F radicals are generated, and the F radicals react with the substrate 12 and the substrate 12 is etched chemically.

At this time, when a high frequency is applied to the substrate 12, a negative bias voltage is generated in the substrate 12. As a result, positive ions ($SF_5^+$) contained in the etching gas collide perpendicularly against the substrate 12, and the substrate 12 is then etched physically by the ion impact.

Figure 6B:
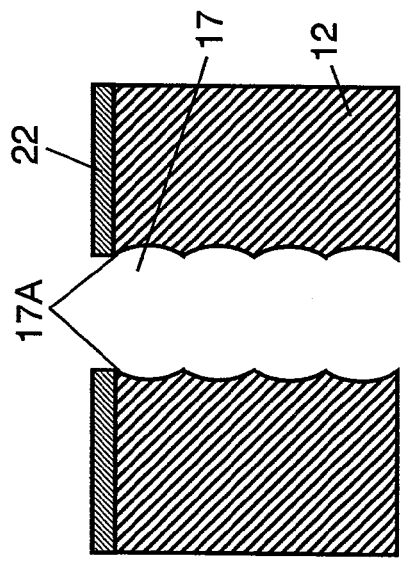
FIG. 6B is an essential sectional view of the same.

As a result, as shown in FIG. 6B, dry etching progresses in perpendicular direction of the substrate 12 (downward).

On the other hand, when suppressing gas $C_4F_8$ is used, high frequency is not applied to the substrate 12. Hence, bias voltage is not generated at all in the substrate 12.

Therefore, $CF^+$ contained in the suppressing gas. $C_4F_8$ sticks to the wall of the dry etching hole of the substrate 12 without being deflected, and a uniform film is formed.

Figure 6C:
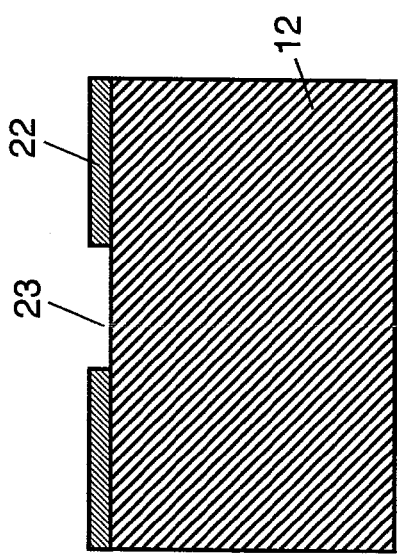
FIG. 6C is an essential sectional view of the same.

This film of $CF^+$ becomes a protective film, and suppresses etching. Herein, the protective film is formed not only in the wall but also in the bottom of the through-hole 17, but the protective film formed in the bottom is easily removed by the ion impact relatively as compared with the protective film formed in the wall, and etching progresses downward. However, in the downward portion where the bottom protective film is removed, etching progresses not only in downward direction but also in lateral direction isotropically, and undulations are formed in the wall of the through-hole 17 as shown in FIG. 6C.

Figure 6D:
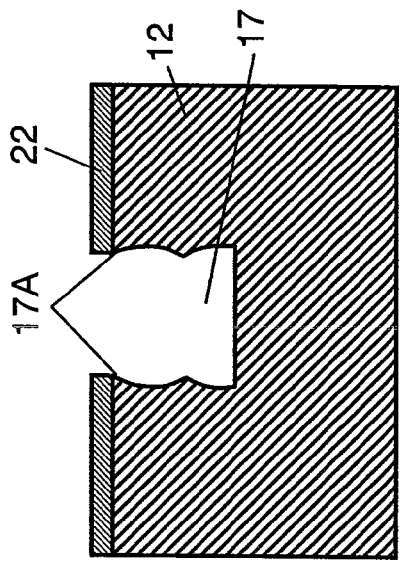
FIG. 6D is an essential sectional view of the same.

Thus, by using the etching gas and suppressing gas alternately, as shown in FIG. 6D, a through-hole 17 having perpendicular undulations in the flow direction of electrolyte solution is formed. The boundary of the inner wall of the through-hole 17 and the surface of the substrate 12 is formed in a sharp corner.

Figure 7:
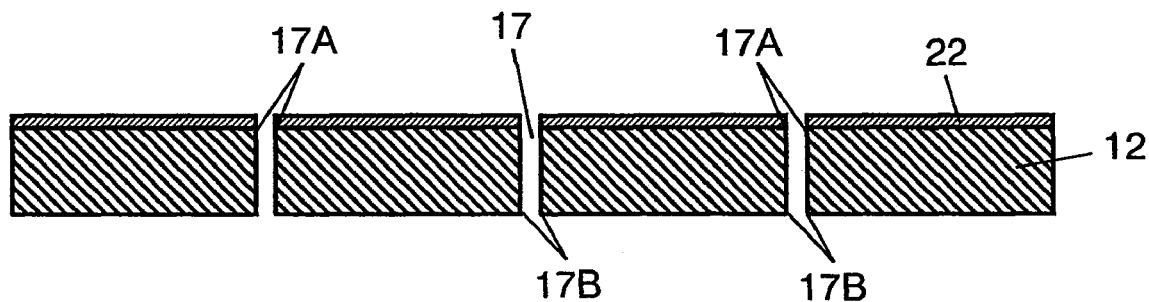
FIG. 7 is a sectional view of manufacturing process of substrate in a preferred embodiment of the invention.

FIG. 7 is a sectional view of substrate 12 omitting the undulations of the through-hole 17. Alternatively, $CF_4$ may be used as etching gas, and $CHF_3$ as suppressing gas.

Figure 8:
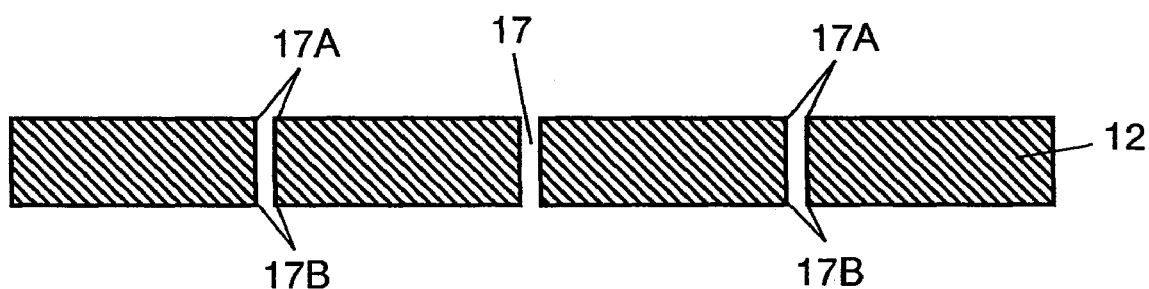
FIG. 8 is a sectional view of manufacturing process of the substrate.

Later, as shown in FIG. 8, the resist mask 22 is removed, and the substrate 12 is heated (annealed) to 1000° C. or more in the atmosphere of decompressed rare gas, hydrogen gas or nitrogen gas.

Figure 9:
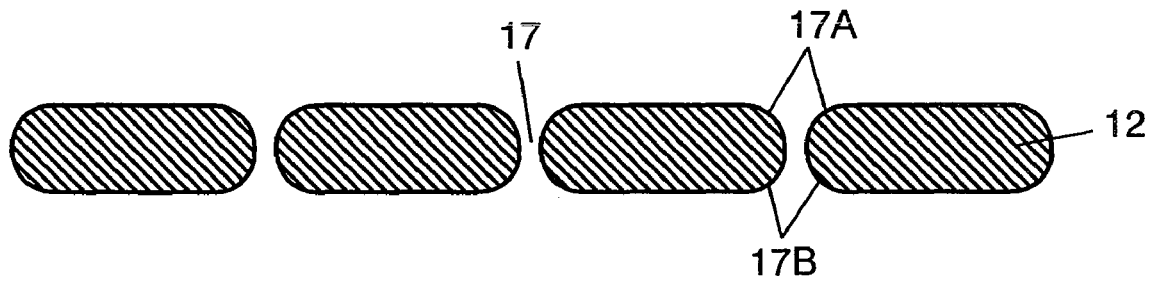
FIG. 9 is a sectional view of manufacturing process of the substrate.
Figure 10:
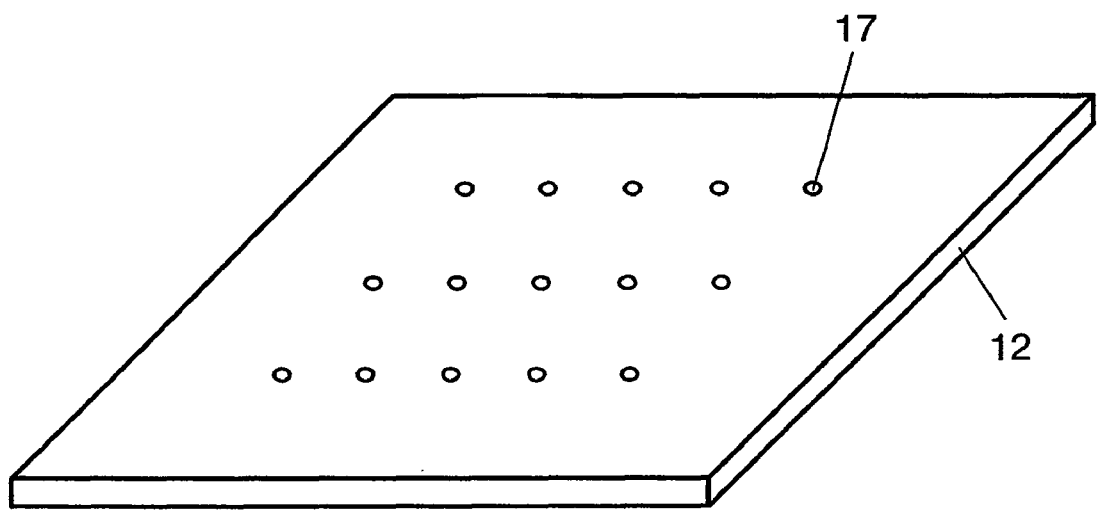
FIG. 10 is a perspective view of substrate in a preferred embodiment of the invention.

As a result, as shown in FIG. 9, the corners of the openings 17A, 17B and the surface of substrate 12 become gradually round.

For example, by raising the heating temperature or extending the heating condition, not only the corners are made round, but also bulges 18A, 18B building up smoothly are formed on the surface of the substrate 12 around the openings 17A, 17B of the through-hole 17 as shown in FIG. 2.

These phenomena can be explained by surface self-diffusion phenomenon of silicon atoms.

The chemical potential of surface atoms is known to be proportional to the surface curvature of substance, and this effect is called Gibbs-Thomson phenomenon.

According to this effect, in the state shown in FIG. 8, since sharp corners are formed in the boundary of the openings 17A, 17B of the through-hole 17 and the surface of the substrate 12, silicon atoms around the openings 17A, 17B are present in a state of high chemical potentiality.

Therefore, in this state, when a sufficient energy is given to silicon atoms to diffuse on the surface, the surface self-diffusion phenomenon is induced in a direction of lowering the chemical potential gradient, and as a result, as shown in FIG. 9, the boundary of the openings 17A, 17B of the through-hole 17 and the surface of the substrate 12 is linked in a round and smooth curved surface.

When the surface self-diffusion reaction progresses, as shown in FIG. 2, in the periphery of the openings 17A, 17B of the through-hole 17, bulges 18A, 18B building up smoothly are formed on the surface of the substrate 12. This is because the condition is stable when the curvature of the curved surface is smaller, and diffusion progresses to draw a smooth curve on the whole from the surface of the substrate 12 to the through-hole 17 as much as possible.

The gas usable at this time is any one of helium, neon, argon, krypton, xenon, hydrogen, and nitrogen, or a mixture thereof. As known from the experiment, when hydrogen is used, in particular, the diffusion speed varies significantly depending on the pressure, and the diffusion can be controlled at high precision, and it is effective in the aspect of the production. The pressure of inert gas atmosphere is preferably controlled under 27 kPa. As a result, a desired shape can be realized at high speed.

When silicon is used as the substrate 12, it is needed to anneal at 1000° C. or higher in order to obtain enough energy for inducing surface self-diffusion phenomenon of silicon.

Such surface self-diffusion phenomenon is obtained in other material than silicon such as $SiO_2$ by varying the annealing condition (the type of inert gas or annealing temperature), and such materials may be also used as the material of the substrate 12.

Non-annealing method includes, for example, chemical vapor deposition method (CVD method) of forming films of silicon or other material sequentially from the upside to downside of the substrate 12, and a similar shape is obtained. In such technique, various materials other than silicon can be selected, and a configuration in consideration of affinity of cell and substrate 12 may be realized.

The effect of the cell electrophysiological sensor in preferred embodiment 1 is explained.

The cell electrophysiological sensor 11 in preferred embodiment 1 is capable of enhancing the smoothness of flow of electrolyte solution (first electrolyte solution 20 and second electrolyte solution 21) flowing in and out of the through-hole 17, thereby enhancing the trapping rate of sample cells 19. The reason is explained below.

That is, when the sectional area of the passage changes suddenly, eddy flow or counter-flow occurs, and the resistance loss of the fluid is increased, and the flow of the electrolyte solution (first electrolyte solution 20 and second electrolyte solution 21) is disturbed.

In the invention, on the other hand, the openings 17A, 17B of the through-hole 17 and the inner wall of the through-hole 17 are formed in a smooth curved surface curved at the inner side of the through-hole 17, as mentioned above, from the surface of the substrate 12 toward the inside of the through-hole 17. In this configuration, from the first electrode jar 13 to the inside of the through-hole 17, and from the inside of the through-hole 17 to the second electrode jar 15, the sectional area change of the passage is made moderate and the resistance loss of the fluid is reduced. As a result, the electrolyte solution (first electrolyte solution 20 and second electrolyte solution 21) flowing in and out of the through-hole is smooth in flow, and the sample cell 19 is sucked accurately, and the trapping rate into the opening 17A is enhanced.

Moreover, the openings 17A, 17B of the through-hole 17 and the inner wall of the through-hole 17 are formed in a smooth surface of square average roughness of Rq=1.0 nm or less, the friction resistance of electrolyte solution (first electrolyte solution 20 and second electrolyte solution 21) is decreased, and the solution flows more smoothly.

Further, by decreasing bubbles inside the through-hole 17, measuring errors of the cell electrophysiological sensor 11 can be suppressed.

That is, in the prior art, when a fine through-hole 17 is formed, undulations are formed in the inner wall of the through-hole 17, and bubbles are likely to be formed inside the through-hole 17, and these bubbles cause to vary the resistance value, often resulting in measuring errors. If the bubbles completely clog the through-hole 17, the first electrode jar 13 and second electrode jar 15 are completely isolated, and measurement is disabled.

In preferred embodiment 1, on the other hand, undulations are removed by annealing process, and the surface is smooth in square average roughness of Rq=1.0 nm or less, and, forming of bubbles can be suppressed. If bubbles are formed slightly, they can be removed by moving along a smooth flow of electrolyte solution (first electrolyte solution 20 and second electrolyte solution 21).

Still more, the inner wall of the through-hole 17 is in a curved surface being curved to the inner side of the through-hole 17, and projecting outward near the central point of the through-hole 17, and the inside diameter of the through-hole 17 is increased gradually from the central point of the through-hole 17 toward the openings 17A, 17B of the through-hole 17.

Accordingly, the flow velocity reaches the maximum at the central point of the through-hole 17, and bubbles are forced out by its water pressure. Since it is hard to remove bubbles in the inner parts of the through-hole 17, this structure is very useful for decreasing the bubbles.

Since the bulge 18B is formed around the opening 17B of the through-hole 17 at the downside of the substrate 12, measuring errors can be decreased. This is considered because, generally, the bubbles forced out from the through-hole 17 stick to the downside of the substrate 12, which cause measuring errors by increase of resistance component, but by forming the bulge 18B, the bubbles can be released to the second electrode jar 15 along the slope of the bulge 18B.

Moreover, since the sample cell is trapped along the curved surface of the opening 17A, the contact tightness of the sample cell 19 and the opening 17A of the through-hole 17 is increased, and it is easy to maintain the tight state, so that the measuring precision of the cell electrophysiological sensor 11 may be enhanced.

This is because the opening 17A of the through-hole 17 is formed in a smooth surface of square average roughness of Rq=1.0 nm or less, and a similar smooth bulge 18A of square average roughness of Rq=1.0 nm or less is formed on the upside of the substrate 12.

By such surface shape, the contact tightness of the sample cell 19 and the opening 17A of the through-hole 17 is increased, and a high sealing performance is obtained. Further, by the bulge 18A, the contact area of the sample cell 19 and the opening 17A is increased. In addition, by setting the distance r1 from the outermost circumference of the bulge 18A to the center of the opening 17A of the through-hole 17 shorter than the radius of the sample cell 19, the contact area of the opening 17A and the sample cell 19 can be further increased.

As a result, the sample cell 19 is accurately held tightly to the opening 17A, and the measuring precision of the cell electrophysiological sensor 11 can be enhanced.

In preferred embodiment 1, the bulge 18A is formed at the upside of the substrate 12 and the bulge 18B at the downside, but as shown in the sectional view in FIG. 9 and the perspective view in FIG. 10, if neither bulge 18A nor 18B is formed, by forming the openings 17A, 17B on a curved surface linking with the surface of the substrate 12, the electrolyte solution flows smoothly, bubbles are decreased, and the contact tightness of the cell and the opening 17A of the through-hole 17 can be enhanced.

Preferred Embodiment 2

Figure 11:
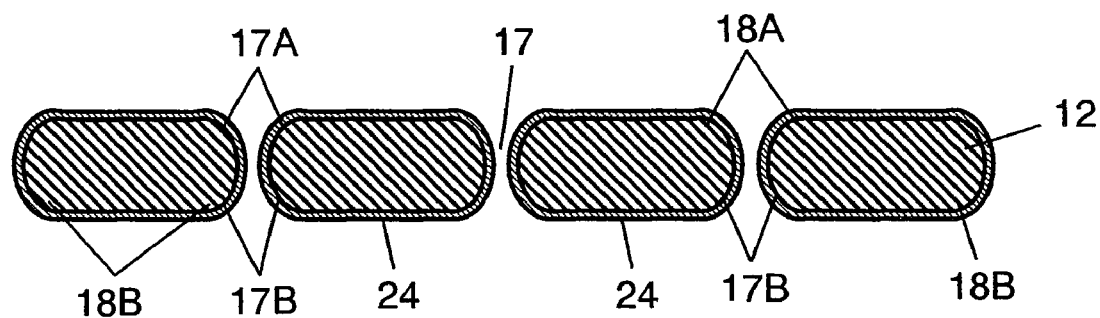
FIG. 11 is a sectional view of substrate in a preferred embodiment of the invention.

A cell electrophysiological sensor in preferred embodiment 2 of the invention is described while referring to the drawing. FIG. 11 is a sectional view of a substrate of cell electrophysiological sensor in preferred embodiment 2.

The configuration of the substrate 12 used in the cell electrophysiological sensor in preferred embodiment 2 is as shown in FIG. 11, in which the both sides of the substrate 12 and the inner wall surface of the through-hole 17 are covered with an insulating layer 24.

In such configuration, when the sample cell 19 is held tightly at the opening 17A of the through-hole 17, the first electrode jar 13 and second electrode jar 15 are completely isolated electrically except for the passage to the sample cell 19.

As the insulating film 24, when a hydrophilic material is used such as silicon oxide or silicon nitride, since the sample cell 19 also has a hydrophilic surface containing hydroxyl group, the sample cell 19 can be held tightly in the opening 17A.

As a result, the hydrophilic property is enhanced in the portion contacting with the electrolyte solution (first electrolyte solution 20 and second electrolyte solution 21), and bubbles can be effectively suppressed.

When a silicon substrate 12 is used as the substrate 12, the insulating layer 24 formed of silicon oxide or silicon nitride can be manufactured easily by oxidizing process or nitriding process, and the productivity is enhanced at the same time.

Preferred Embodiment 3

Figure 12:
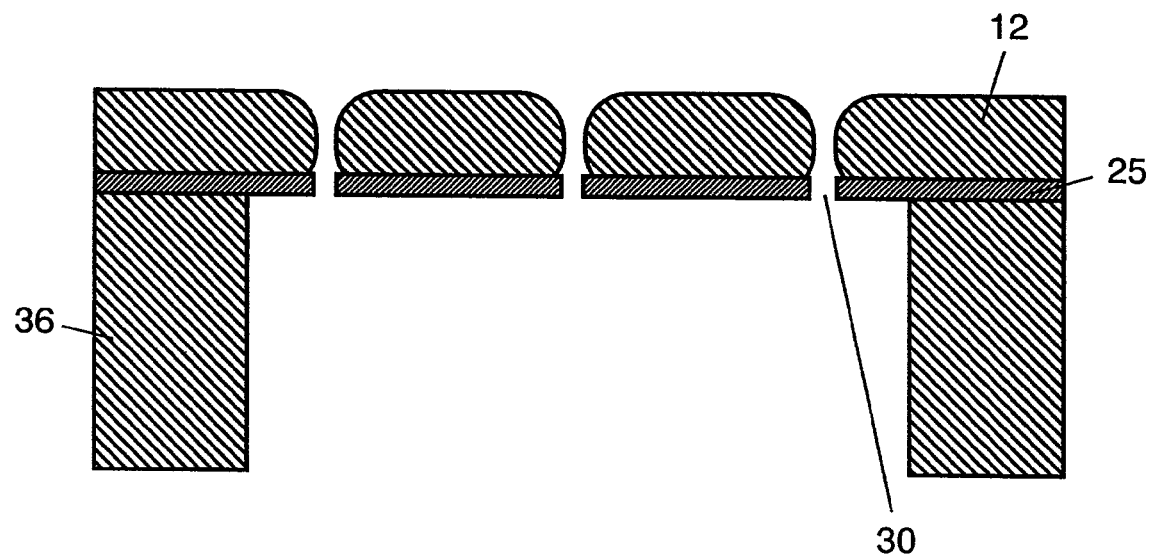
FIG. 12 is a sectional view of chip in a preferred embodiment of the invention.

Preferred embodiment 3 differs from preferred embodiment 1 in that a silicon oxide layer is laminated as oxide layer 25 preliminarily at one side of the substrate 12 as shown in a sectional view of a chip 36 shown in FIG. 12.

Figure 13:
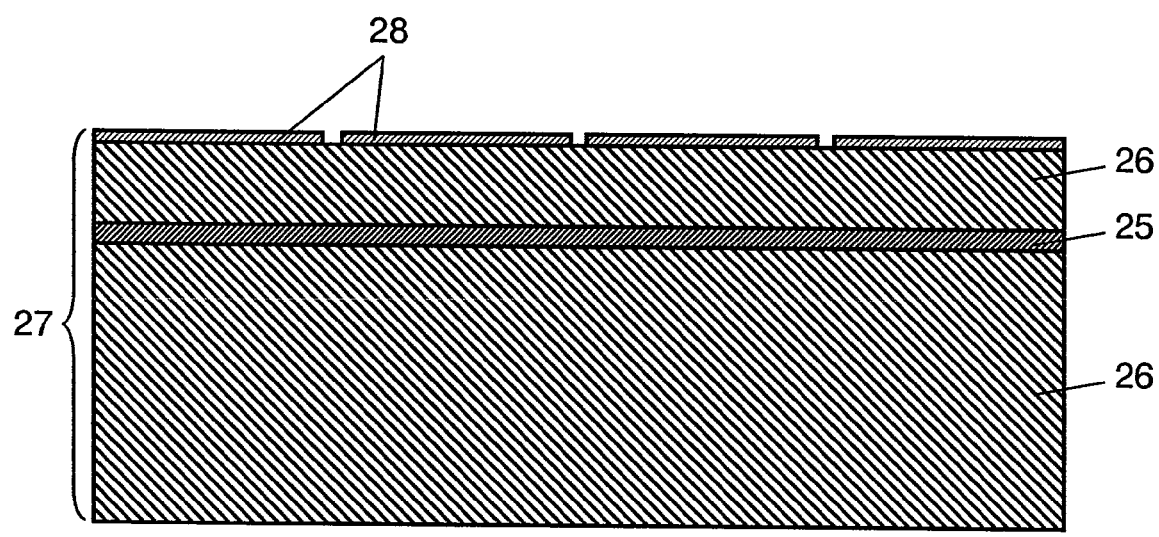
FIG. 13 is a sectional view of manufacturing process of chip in a preferred embodiment of the invention.
Figure 14:
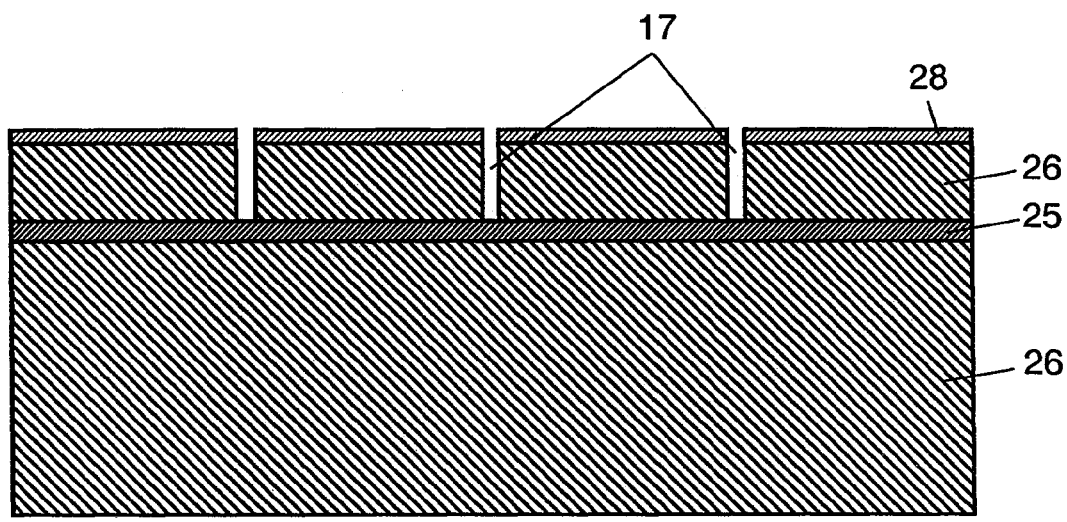
FIG. 14 is a sectional view of manufacturing process of the chip.

In preferred embodiment 3, as shown in FIG. 13, in a block 27 in which the oxide layer 25 is enclosed with a silicon layer 26, a resist mask 28 having a hole is formed, and as shown in FIG. 14, a through-hole 17 is formed by etching from the side of the silicon layer 26 of the substrate 12. In FIG. 13 and FIG. 14, the upper silicon layer 26 of two silicon layers 26 becomes the substrate 12 as shown in FIG. 12.

At this time, since the oxide layer 25 (silicon oxide) is lower in etching rate than the silicon layer 26, by etching from the silicon layer 26, etching stops at the oxide layer 25, and the depth of the through-hole 17 and thickness of the substrate 12 (substrate 12 in FIG. 12) can be managed at high precision.

Consequently, by dry etching, a hole 30 (hole 30 in FIG. 12) is formed at a position corresponding to the through-hole 17 of the oxide layer 25. A proper gas for etching the oxide layer 25 is, for example, $CF_4$.

Figure 15:
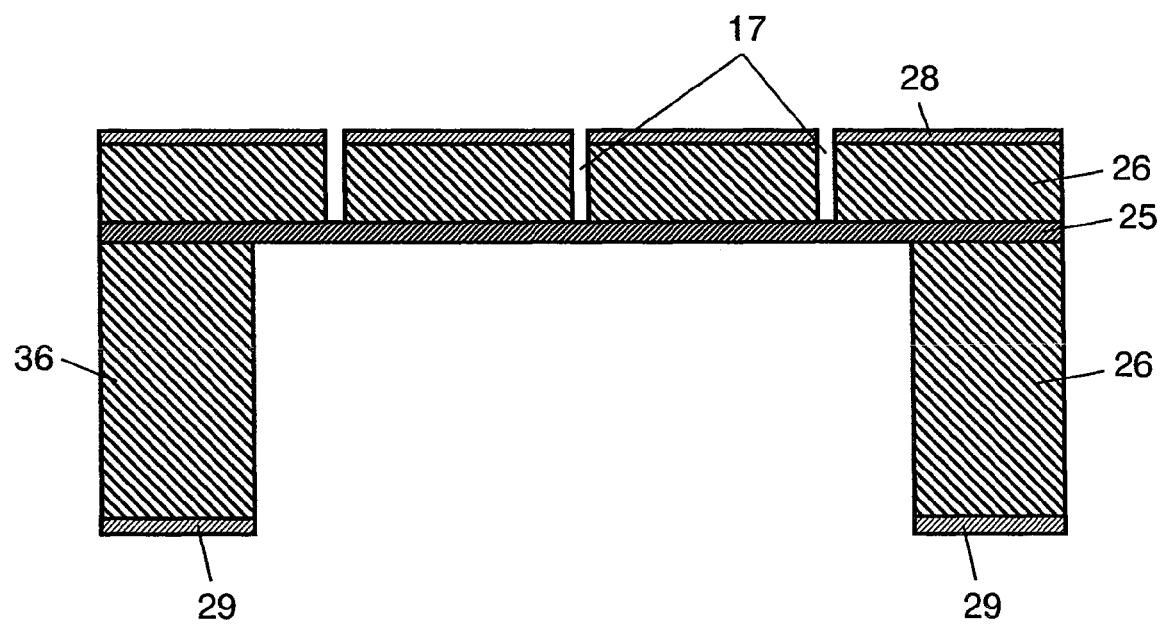
FIG. 15 is a sectional view of manufacturing process of the chip.

Then, as shown in FIG. 15, a resist mask 29 is formed on the silicon layer 26, and the silicon layer 26 is etched.

Finally, in the atmosphere of rare gas, nitrogen gas or hydrogen gas, the substrate 12 is heated, or films are formed by vapor phase method from both sides of the substrate 12, and the chip 36 shown in FIG. 12 is formed.

The oxide layer 25 may be also positioned at the upside of the substrate 12, that is, at the side of trapping the sample cell, or may be disposed at the downside of the substrate 12. In particular, when desired to suck the fluid from beneath the substrate 12, the oxide layer 25 may be also positioned at the upside of the substrate 12, or when desired to improve flow above the substrate, the oxide layer 25 may be also positioned at the downside of the substrate 12.

Figure 16:
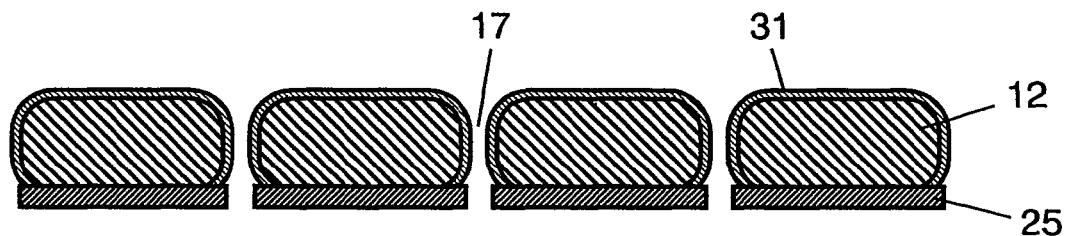
FIG. 16 is a sectional view of substrate in a preferred embodiment of the invention.

Further, as shown in FIG. 16, at one side of the substrate 12, that is, at the side not forming the oxide layer 25 and in the inner wall of the through-hole 17, when an insulating layer 31 is formed, an electric insulation above and beneath the substrate 12 can be enhanced.

Figure 17:
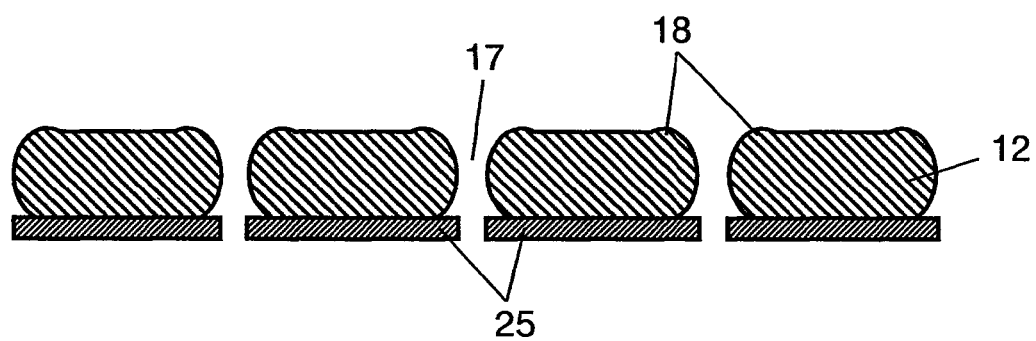
FIG. 17 is its sectional view.

Or, a bulge 18 may be formed as shown in FIG. 17.

Explanation is omitted about same structure and effects as in the other preferred embodiments.

Preferred Embodiment 4

Figure 18:
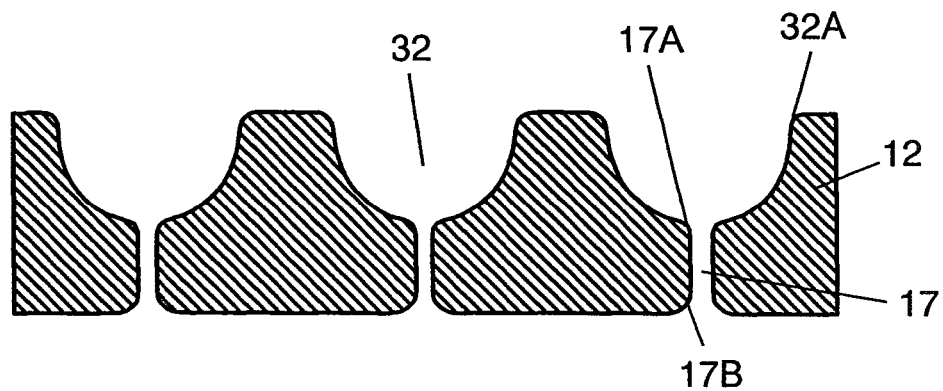
FIG. 18 is its sectional view.

As shown in FIG. 18, the substrate 12 used in the cell electrophysiological sensor 11 in preferred embodiment 4 includes a recess 32 formed in the upside (first side) of the substrate 12, and a through-hole 17 penetrating from the recess 32 to the downside (second side) of the substrate 12.

Openings 17A, 17B of the through-hole 17 are formed in a smooth curved surface, and the upside of the substrate 12 and the inner wall of the recess 32, the inner wall of the recess 32 and the inner wall of the through-hole 17, and the inner wall of the through-hole 17 and the downside of the substrate 12 are respectively linked in a curved surface. In preferred embodiment 4, the surface and inner wall of the openings 17A, 17B of the through-hole 17 and the inner wall of the recess 32 are formed in square average roughness of $Rq=1.0$ nm or less.

In preferred embodiment 4, the recess 32 spreads outward from the opening 17A of the through-hole 17, and is formed in a curved surface linking to the upside of the substrate 12, and the through-hole 17 is formed from the deepest position of the recess 32.

In the preferred embodiment, the shape of the recess 32 is hemispherical or nearly hemispherical. By the hemispherical or nearly hemispherical shape, when the sample cell is a true sphere, the cell can be held easily without being distorted. When the size of the sample cell is about 5 to 50 μm, the diameter of the opening 32A of the recess 32 is desired to be about 30 μm.

A manufacturing method of cell electrophysiological sensor 11 of the preferred embodiment is explained below.

Figure 19:
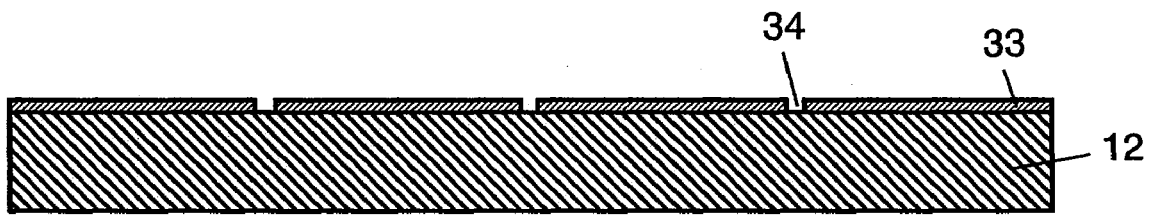
FIG. 19 is a sectional view of manufacturing process of substrate in a preferred embodiment of the invention.

As shown in FIG. 19, a resist mask 33 is formed on the upside of the silicon substrate 12. At this time, a mask hole 34 of nearly same shape as the section of desired through-hole 17 is patterned.

Figure 20:
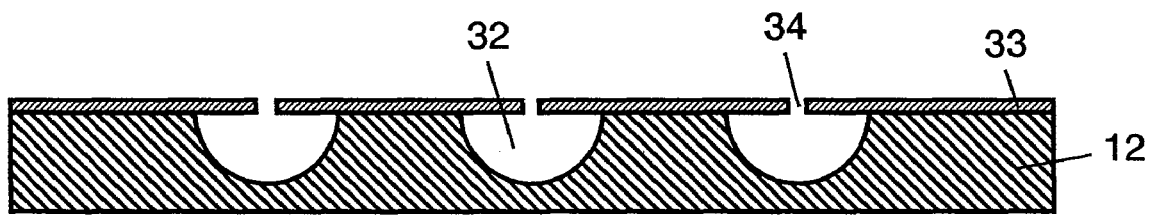
FIG. 20 is a sectional view of manufacturing process of the substrate.

Next, as shown in FIG. 20, by etching the substrate 12, a recess 32 is formed. The etching method at this time is desired to be dry etching of high precision and fine processing. A desired etching gas is $SF_6$, $CF_4$, $NF_3$, $XeF_2$, or mixed gas thereof. These gases are effective to promote silicon etching not only in the depth direction but also in the horizontal direction, and the substrate 12 can be etched precisely in a bowl shape. In preferred embodiment 4, the etching promoting gas is mixed with carrier gas such as $N_2$, Ar, He, or $H_2$.

Figure 21:
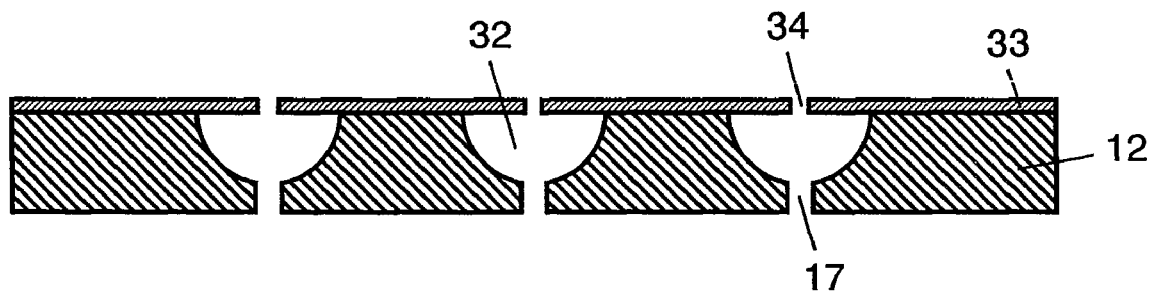
FIG. 21 is a sectional view of manufacturing process of the substrate.

In consequence, as shown in FIG. 21, after the resist mask 33 is disposed as specified, a through-hole 17 is formed to penetrate in the perpendicular direction from the bottom of the recess 32 to the downside of the substrate 12.

At this time, same as in preferred embodiment 1, dry etching is processed by using etching gas and suppressing gas alternately.

Finally, the resist mask 33 is removed, and the substrate 12 is heated at 1000° C. or higher in decompressed inert gas atmosphere same as in preferred embodiment 1, and the substrate 12 (FIG. 18) having a smooth curvature of preferred embodiment 4 is manufactured.

Instead of heating (annealing), alternatively, films of same shape can be formed by vapor phase method same as in preferred embodiment 1.

Effects of preferred embodiment 4 are described below.

In preferred embodiment 4, as shown in FIG. 18, the upside of the substrate 12 and the inner wall of the recess 32, the inner wall of the recess 32 and the inner wall of the through-hole 17, and the inner wall of the through-hole 17 and the downside of the substrate 12 are respectively linked in a curved surface. As a result, sudden sectional area changes of passage are suppressed, the resistance loss of fluid is decreased, the flow of electrolyte solutions 20, 21 (see FIG. 3) flowing in and out of the through-hole 17 is made smoother, and the trapping rate of sample cells is enhanced, and the measuring precision of the cell electrophysiological sensor 11 is improved.

In preferred embodiment 4, the surface and inner wall of the openings 17A, 17B of the through-hole 17 and the inner wall of the recess 32 are formed in square average roughness of $Rq=1.0$ nm or less, and the resistance loss of fluid is further reduced, bubbles are suppressed, and the trapping rate of sample cells is increased.

Further, by forming the recess 32 at the upside of the substrate 12, it is easier to trap the sample cell 19, and it is easier to maintain the trapped sample cell 19.

Besides, the contact area of the opening 17A of the through-hole 17 and the sample cell 19 is increased, and the contact tightness of the opening 17A of the through-hole 17 and the sample cell 19 is improved.

In preferred embodiment 4, since the through-hole 17 is formed at the deepest position of the recess 32, it is easier to align the sample cell 19 trapped in the recess 32 into the opening 17A of the through-hole 17. As a result, the trapping rate of sample cells is increased.

Figure 22:
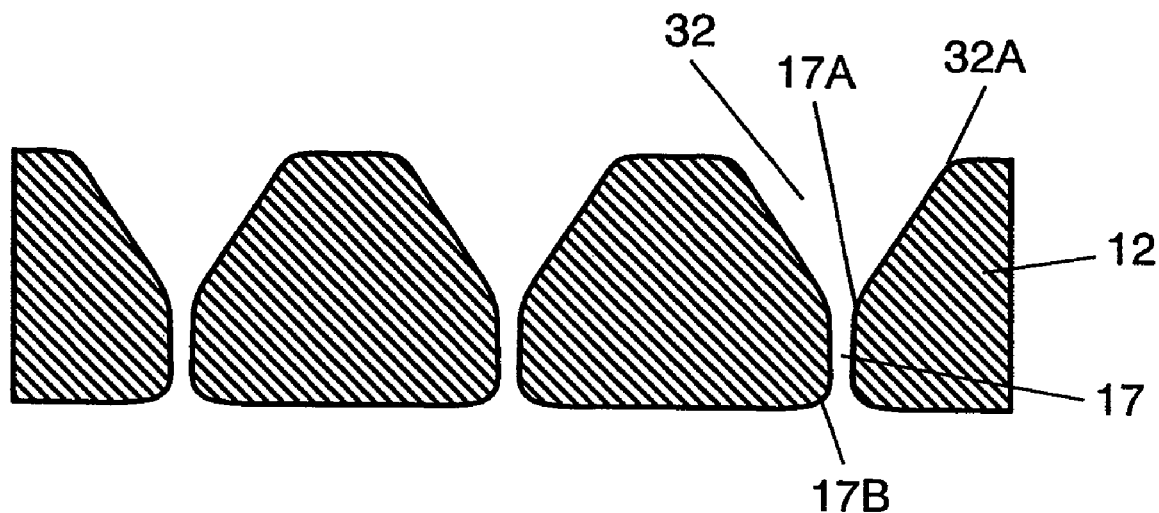
FIG. 22 is a sectional view of substrate in a preferred embodiment of the invention.

In preferred embodiment 4, meanwhile, the recess 32 is hemispherical, but the recess 32 may formed in other shape, as shown in FIG. 22, such as conical or nearly conical shape. In particular, when the recess 32 is formed in conical or nearly conical shape, if the slope of the recess 32 is steep and the sample cell is a sticky cell, the cell can be trapped efficiently in the through-hole 17 without being stuck somewhere in the recess 32.

Moreover, when an insulating layer (not shown) is formed between the surface of the substrate 12 shown in FIG. 18, and the recess 32 and inner wall of the through-hole 17, an electric insulation is enhanced between the upside and downside of the substrate 12.

Or, an oxide layer (not shown) may be laminated preliminarily on the downside (second side) of the substrate 12. As a result, the thickness off the substrate 12 can be managed at high precision. In this case, an insulating layer (not shown) may be formed between the upside of the substrate 12, the recess 32 and inner wall of the through-hole 17.

A bulge (not shown) building up outward may be formed on the outer circumference of the openings 17A, 17B of the through-hole 17. As a result, the contact area of the sample cell 19 and the opening 17A is increased, and bubbles staying in the opening 17B of the through-hole 17 may be decreased.

Figure 23:
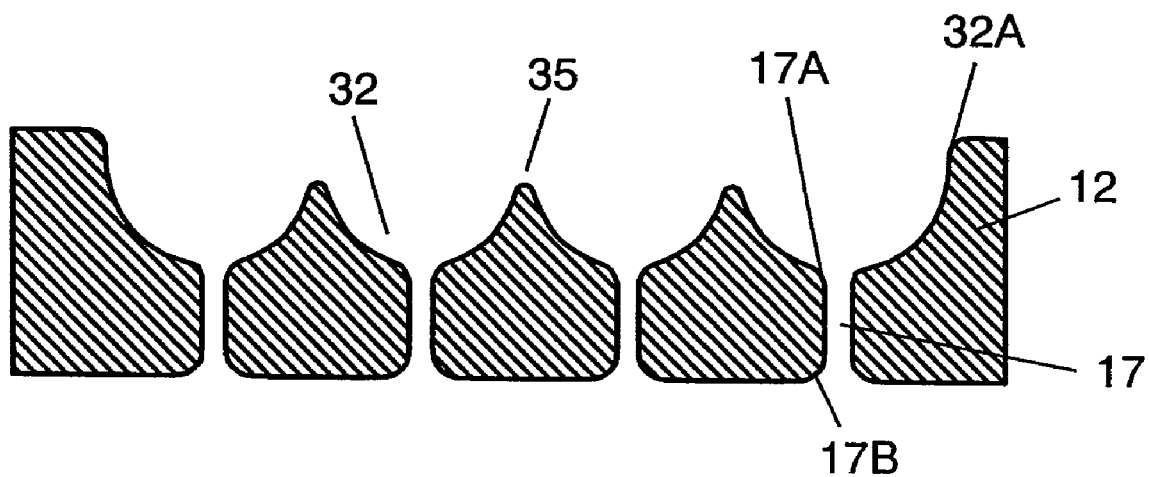
FIG. 23 is its sectional view.

As shown in FIG. 23, multiple recesses 32 may be formed on the upside of the substrate 12, and the inner walls of the adjacent recesses 32 may be crossed each other. As a result, on the upside of the substrate 12, there is almost no flat part in the region of forming the recesses 32, and if the sample cell contacts with the intersection 35, it is not stuck, and is inclined to either recess 32 by gravity, and is aligned to the center of the recess 32 along the inner wall.

The intersection 35 may be formed in a smooth curved surface by annealing or other process, and the contacting sample cell can be safely guided into the opening 17A of the through-hole 17 without being injured.

In FIG. 23, by setting the distance between central points of adjacent through-holes 17 somewhat shorter than two times of the average diameter of the sample cell, plural cells are prevented from being trapped in one recess 32.

In FIG. 23, by setting the distance between central points of adjacent through-holes 17 longer than the average diameter of the sample cell, contact of sample cells held in one recess can be decreased. As a result, the measuring precision of the cell electrophysiological sensor 11 is improved.

In preferred embodiment 4, explanation is omitted about same structure and effects as in the other preferred embodiments.

Preferred Embodiment 5

Figure 24:
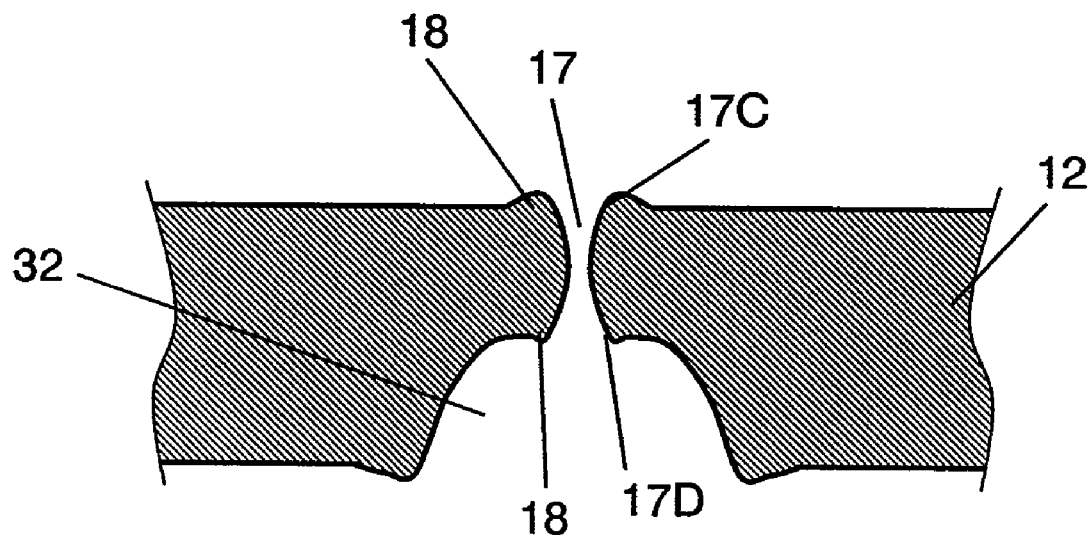
FIG. 24 is its sectional view.

As shown in FIG. 24, preferred embodiment 5 is similar to preferred embodiment 4 except that the substrate is turned upside down.

That is, the substrate 12 used in the cell electrophysiological sensor 11 of preferred embodiment 5 includes a recess 32 formed at the downside of the substrate 12, and a through-hole 17 penetrating from the recess 32 to the upside of the substrate 12.

Openings 17C, 17D of the through-hole 17 are formed in a smooth curved surface, and the downside of the substrate 12 and the inner wall of the recess 32, the inner wall of the recess 32 and the inner wall of the through-hole 17, and the inner wall of the through-hole 17 and the upside of the substrate 12 are respectively linked in a curved surface.

In preferred embodiment 5, the surface and inner wall of the openings 17C, 17D of the through-hole 17 and the inner wall of the recess 32 are formed in square average roughness of Rq=1.0 nm or less.

In preferred embodiment 5, the recess 32 spreads outward from the opening 17D of the through-hole 17, and is formed in a curved surface linking to the downside of the substrate 12, and the through-hole 17 is formed from the deepest position of the recess 32.

In preferred embodiment 5, since the sectional area of the passages is changed in gradual steps from the through-hole 17 to the recess 32, from the recess 32 to the second electrode jar (15 in FIG. 1) beneath the substrate 12, the resistance loss of the fluid is smaller. Further, since the downside of the substrate 12 and the inner wall of the recess 32, the inner wall of the recess 32 and the inner wall of the through-hole 17, and the inner wall of the through-hole 17 and the upside of the substrate 12 are respectively linked in a curved surface, the fluid resistance can be further reduced.

In preferred embodiment 5, since the recess 32 is formed beneath the substrate 12, it is easier to suck the second electrolyte solution 21 (second electrode 21 in FIG. 1) from beneath the substrate 12, and the contact tightness of the sample cell 19 and the opening 17C of the through-hole 17 is enhanced. Besides, since the recess 32 is formed beneath the substrate 12, it is easier to distribute the medicine (such as Nystatin) injected from beneath the substrate 12 into the through-hole 17.

By forming an insulating layer (not shown) between the surface of the substrate 12, and the recess 32 and inner wall of the through-hole 17, an electric insulation is enhanced between the first electrode jar 13 and second electrode jar 15 shown in FIG. 1.

Figure 25:
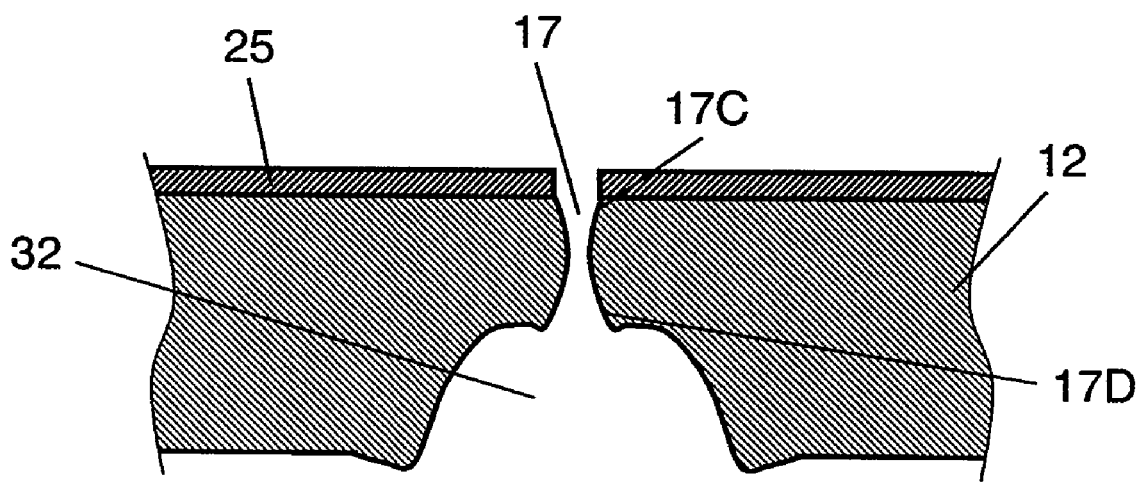
FIG. 25 is its sectional view.
Figure 26:
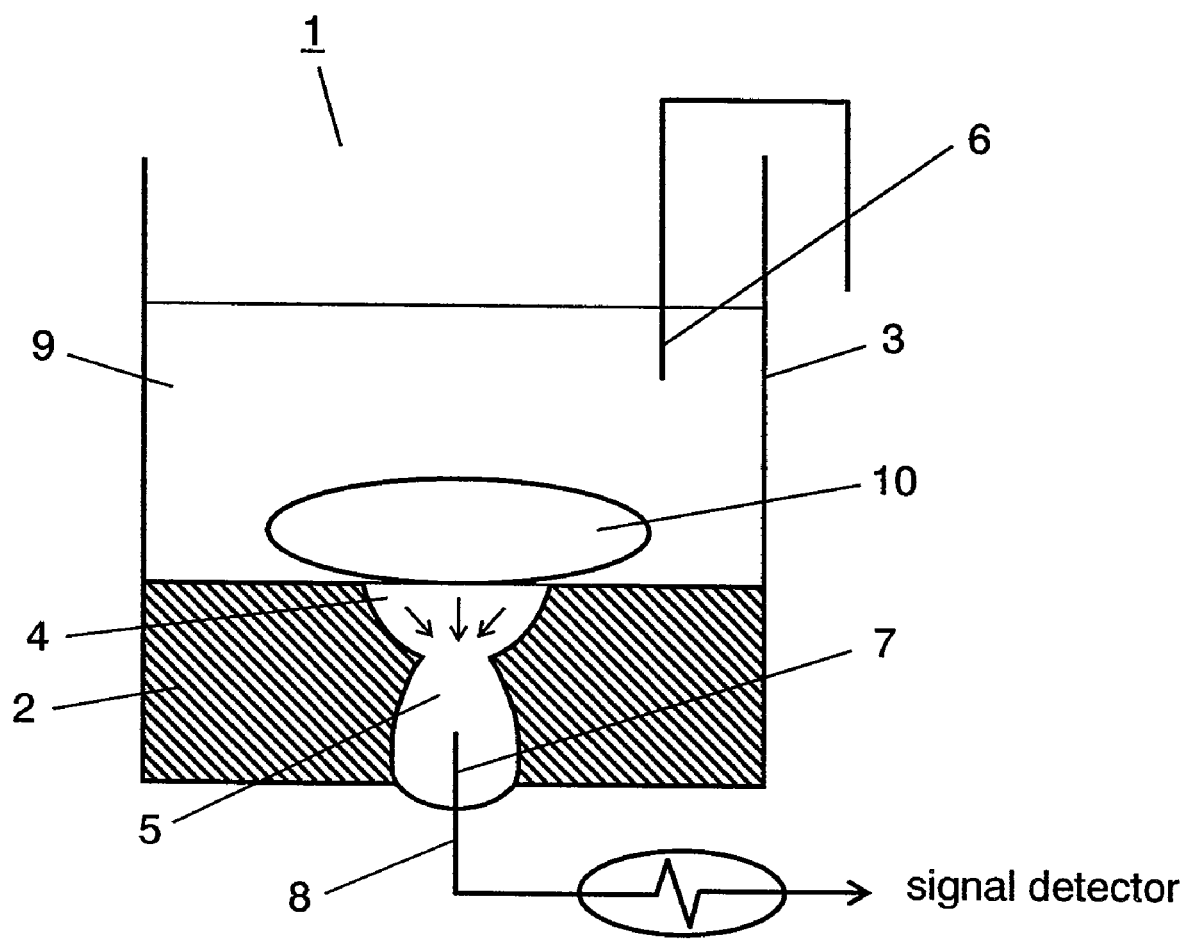
FIG. 26 is a sectional view of cell electrophysiological sensor in a prior art.

Or, as shown in FIG. 25, preliminarily, the oxide layer 25 may be laminated on the upside of the substrate 12. Hence, the thickness of the substrate 12 can be managed at high precision. In this case, an insulating layer (not shown) may be formed on the downside of the substrate 12 and the recess 32 and the inner wall of the through-hole 17.

On the outer circumference of the openings 17C, 17D of the through-hole 17, the bulge 18 building up outward may be formed. When the bulge 18 is formed above the through-hole 17, it is easier to trap the sample cell 19 in the opening 17C, and the contact area of the sample cell 19 and the opening 17C increases. Or when the bulge 18 is formed beneath the through-hole 17, bubbles staying in the opening 17D can be decreased.

In preferred embodiment 5, explanation is omitted about same structure and effects as in the other preferred embodiments.

INDUSTRIAL APPLICABILITY

As described herein, the cell electrophysiological sensor of the invention is capable of sucking the cells accurately, and trapping and holding precisely in the opening of the through-hole, and is hence very useful in the field of medical and biological applications where measurement of high precision and high efficiency is demanded.

The invention claimed is:

1. A chip for cell electrophysiological sensor comprising a substrate,
   wherein the substrate has a through-hole penetrating from an upside to a downside thereof, and
   an inner wall of the through-hole comprises a curved surface, the curved surface forming a smooth transition with a surface of the substrate
   wherein a surface and an inner wall of an opening of the through-hole are formed in square average roughness of Rq=1.0 nm or less.

2. The chip for cell electrophysiological sensor of claim 1, wherein an oxide layer is formed on the substrate.

3. The chip for cell electrophysiological sensor of claim 1, wherein the curved surface is curved to an inner side of the through-hole, and an inside diameter of the through-hole is formed to be larger gradually from a side of the through-hole toward the opening of the through-hole.

4. The chip for cell electrophysiological sensor of claim 1, wherein an inside diameter of the through-hole is formed to be minimum at a central point of the through-hole in a depth direction of the through-hole, and to be larger gradually from the central point toward an opening of the through-hole.

5. The chip for cell electrophysiological sensor of claim 1, wherein an outer circumference of an opening of the through-hole has a bulge building up smoothly outward.

6. The chip for cell electrophysiological sensor of claim 1, wherein an outer circumference of an opening of the through-hole has a bulge building up smoothly outward, and a distance from an outermost circumference of the bulge to a center of the opening of the through-hole on the substrate is shorter than a radius of a cell to be measured.

7. The chip for cell electrophysiological sensor of claim 1, wherein the substrate is formed of silicon.

8. A cell electrophysiological sensor comprising:
   a chip for cell electrophysiological sensor according to claim 1,
   electrode jars disposed above and beneath the substrate of the chip for the cell electrophysiological sensor, and
   electrodes electrically connected to a solution contained in the electrode jars.

9. The chip for cell electrophysiological sensor according to claim 1,
   wherein the substrate is provided with a recess formed in the upside of the substrate, and the through-hole extends from the recess toward the downside opposite to the upside of the substrate, and
   the upside of the substrate and an inner wall of the recess, the inner wall of the recess and the inner wall of the through-hole, and the inner wall of the through-hole and the downside of the substrate are respectively linked by the curved surface.

10. The chip for cell electrophysiological sensor of claim 9, wherein the recess spreads outward from an opening of the through-hole, and is formed in the curved surface linking with the upside of the substrate.

11. The chip for cell electrophysiological sensor of claim 9, wherein the recess is hemispherical.

12. The chip for cell electrophysiological sensor of claim 9, wherein the recess is conical.

13. The chip for cell electrophysiological sensor of claim 9, wherein the substrate has an oxide layer in the downside.

14. The chip for cell electrophysiological sensor of claim 9, wherein the inner wall of the through-hole is formed in the curved surface curved to an inner side of the through-hole, and an inside diameter of the through-hole is formed to be increased gradually from the inner inside of the through-hole toward the opening of the through-hole.

15. The chip for cell electrophysiological sensor of claim 9, wherein an inside diameter of the through-hole is formed to be minimum at a central point in a depth direction of the through-hole, and increased gradually from the central point toward an opening of the through-hole.

16. The chip for cell electrophysiological sensor of claim 9, wherein the outer circumference of an opening of the through-hole has a bulge building up smoothly outward.

17. The chip for cell electrophysiological sensor of claim 9, wherein an outer circumference of an opening of the through-hole has a bulge building up smoothly outward, and a distance from an outermost circumference of the bulge to a center of an opening of the through-hole on the substrate is shorter than a radius of a cell to be measured.

18. The chip for cell electrophysiological sensor of claim 9, wherein the substrate is formed of silicon.

19. A cell electrophysiological sensor comprising:
   a chip for cell electrophysiological sensor according to claim 9,
   electrode jars disposed above and beneath the substrate of the chip for the cell electrophysiological sensor, and
   electrodes electrically connected to a solution contained in the electrode jars.

* * * * *